United States Patent [19]

Fujiyama et al.

[11] Patent Number: 4,460,794
[45] Date of Patent: Jul. 17, 1984

[54] PROCESS FOR CONTINUOUS PRODUCTION OF ALKYLBENZALDEHYDES

[75] Inventors: Susumu Fujiyama; Shunichi Matsumoto, both of Kurashiki, Japan

[73] Assignee: Mitsubishi Gas Chemical Company, Inc., Tokyo, Japan

[21] Appl. No.: 386,588

[22] Filed: Jun. 9, 1982

Related U.S. Application Data

[63] Continuation of Ser. No. 223,782, Jan. 9, 1981, abandoned.

[30] Foreign Application Priority Data

Jan. 10, 1980 [JP] Japan ................................. 55-1652

[51] Int. Cl.³ ............................................. C07C 45/49
[52] U.S. Cl. ................................................ 568/428
[58] Field of Search ....................................... 568/428

[56] References Cited

U.S. PATENT DOCUMENTS 2,485,237 10/1949 Gresham et al. .................. 568/428
3,948,998 4/1976 Fujiyama et al. ................. 568/428

FOREIGN PATENT DOCUMENTS 728212 2/1966 Canada ............................. 568/428
2422197 11/1974 Fed. Rep. of Germany ...... 568/428

*Primary Examiner*—Bernard Helfin
*Attorney, Agent, or Firm*—Armstrong, Nikaido, Marmelstein & Kubovcik

[57] ABSTRACT

Alkylbenzaldehyde is continuously produced in high yield from alkylbenzene by formylation with carbon monoxide in the presence of HF—$BF_3$, where the alkylbenzene, HF—$BF_3$ and carbon monoxide under a carbon monoxide partial pressure of at least 5 kg/cm² absolute are introduced into the reactor to continuously carry out complexing of the alkylbenzene with HF—$BF_3$ and formylation with the carbon monoxide successively in one and same reactor.

7 Claims, 1 Drawing Figure

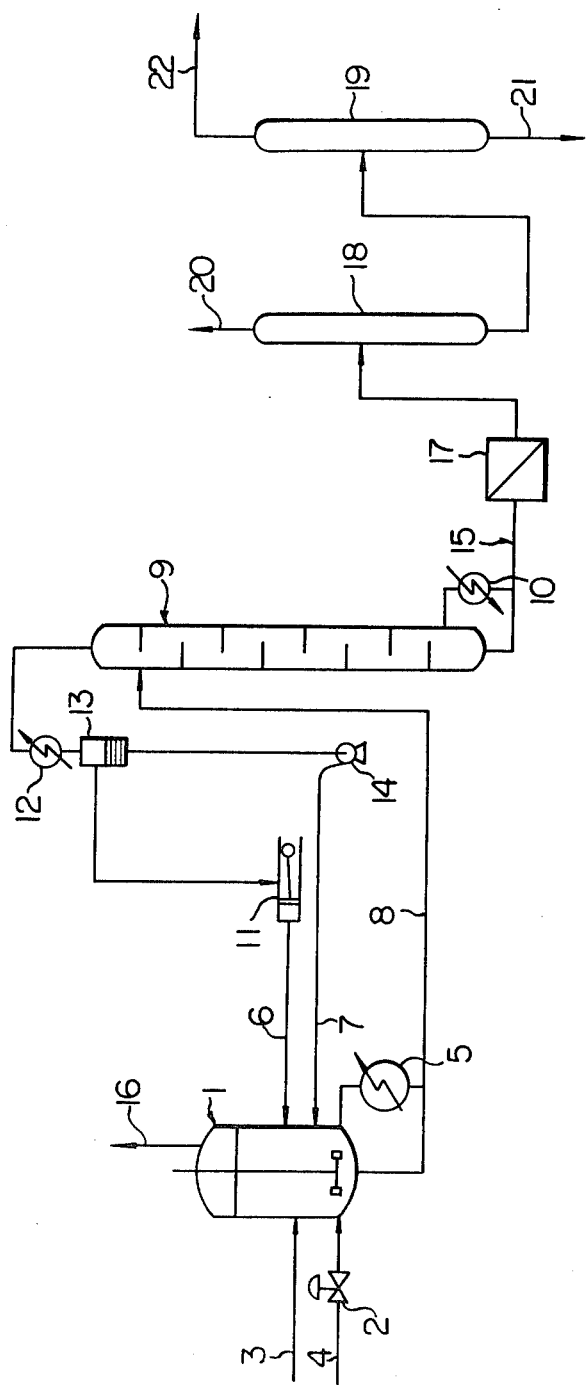

PROCESS FOR CONTINUOUS PRODUCTION OF ALKYLBENZALDEHYDES

This is a continuation of application Ser. No. 223,782, filed Jan. 9, 1981.

This invention relates to a process for continuously producing alkylbenzaldehydes by formylating alkylbenzenes with carbon monoxide, which will be hereinafter referred to as "CO", in the presence of hydrogen fluoride-boron trifluoride, which will be hereinafter referred to as "HF—BF$_3$", and more particularly to a process for continuously producing alkylbenzaldehydes by complexing of alkylbenzenes by HF—BF$_3$ and formylation with CO successively in one and same reactor.

It is known from U.S. Pat. No. 2,485,237 that aromatic aldehydes such as paratolualdehyde, etc. can be produced from aromatic hydrocarbons such as toluene, etc. through reaction with CO in the presence of HF—BF$_3$, and the reaction is regarded as a modification of Gattermann-Koch reaction using hydrogen chloride-aluminum chloride, etc. as a catalyst. U.S. Pat. No. 2,485,237 discloses batch reaction, where CO pressure is so high that the process itself has various problems in commercial practice.

Since then, improvements have been made in the processes, and continuous operation of reaction was succeeded by selection of a ratio of feed hydrocarbon to catalyst at the reaction, etc. (Japanese Patent Publication No. 29760/64), where feed toluene is complexed with HF—BF$_3$ in advance, and then converted to paratolualdehyde through reaction with CO, and HF—BF$_3$ is used in excess of the toluene. The reaction proceeds in the following sequences.

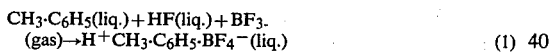

[Complexing with HF—BF$_3$ takes place according to equation (1)].

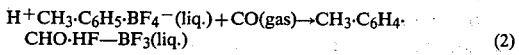

(Formylation according to equation 2).

HF—BF$_3$ complex of feed toluence reacts with CO to form aromatic aldehyde.

In the step (1), reaction with gaseous boron trifluoride, which will be hereinafter referred to as BF$_3$, proceeds, and in the step (2), reaction with gaseous CO proceeds. Both reactions are gas-liquid ones, and formylation of step (2) requires a higher pressure than complexing of step (1). However, the process has such an advantage that supply of a large amount of BF$_3$ gas to the reaction system is unnecessitated by forming toluene-HF—BF$_3$ complexes in advance.

HF—BF$_3$ is a good catalyst for formylation reaction, and also shows a very good catalytic action upon isomerization, disproportionation, etc. of alkylbenzenes at the same time, as disclosed in and well known from J. Am. Chem. Soc. 2411 (1953).

For example, cumene undergoes reaction according to the following equations:

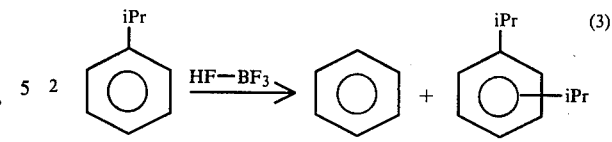

wherein iPr represents isopropyl group, and then,

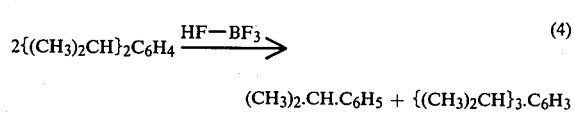

The reaction proceeds very rapidly even at a low temperature such as −20° C., and is very hard to control.

Thus, the process disclosed in Japanese Patent Publication No. 29760/64 is applicable only to the alkylbenzenes that are highly stable by themselves in the presence of HF—BF$_3$, such as toluene.

Examples of producing alkylbenzaldehydes from various feed aromatic compounds were disclosed by Takesaki et al [Sekiyu Gakkai-shi, Vol. 20, No. 8, page 654 (1977)], where there is such a disclosure that, when cumene was used as a feed, the aldehyde yield is as low as 28%.

The present inventors have confirmed that, when aldehyde was produced from cumene as feed according to the ordinary process, only a low yield was likewise obtained, and the product contained diisopropylbenzene, triisopropylbenzene and their formylated products, and thus isolation of desired cuminaldehyde was very difficult to conduct.

Since the make reaction using HF—BF$_3$ is distinguished in yield of para isomers of the resulting aldehydes, reaction rate, etc., the present inventors have made every effort to establish a practical process, and consequently have found a process for producing alkylbenzaldehydes with high purity in high yield from the alkylbenzenes that are unstable in the presence of HF—BF$_3$, and have established the present invention.

According to the present process, it is necessary to continuously supply feed alkylbenzene to a reactor containing a reaction mixture containing HF—BF$_3$, into which CO is introduced under a partial pressure of at least 5 kg/cm$^2$ absolute. This can suppress the side reactions and can make the formylation proceed preferentially.

More specifically, for example, BF$_3$ is dissolved in cooled hydrogen fluoride in a reactor, and CO is introduced at least under the specific pressure and mixed and dissolved therein by stirring, etc. Hydrogen fluoride will be hereinafter referred to as "HF". Then, alkylbenzene is gradually supplied to the reactor to carry out reaction. The alkylbenzene is rapidly converted to formylated product. The CO in the reactor is correspondingly consumed, and thus CO is supplied to the reactor to maintain CO constantly under the specific pressure. Then, withdrawal of the reaction solution from the reactor is started, while supply of alkylbenzene and corresponding HF—BF$_3$ to the reactor is started in a specific ratio, whereby the reaction can proceed in a continuous manner. Undesirable side reaction can be suppressed and a high aldehyde yield can be maintained by maintaining the partial pressure of CO in the reactor at least under the specific pressure in the course of reaction.

Conditions for carrying out the present process will be described in detail below:

In order to obtain good yield, partial pressure of CO in the reactor must be maintained at least under 5 kg/cm$^2$ absolute, preferably 10 kg/cm$^2$ absolute or higher, but the partial pressure over 30 kg/cm$^2$ absolute is not economical and unnecessary. In order to rapidly dissolve CO into the reaction solution, the reaction solution must be stirred to intimately contact CO with the reaction solution.

A feed ratio of the catalyst HF—BF$_3$ to the feed alkylbenzene to the reactor must be maintained in a preferable state, because the presence of HF—BF$_3$ in excess of the feed alkylbenzene is an important factor to the progress of formylation reaction by CO, whereas side reactions such as disproportionation reaction of feed alkylbenzene, etc. is accelerated by the presence of a small amount of HF—BF$_3$, and a maximum acceleration is liable to be attained in a ratio less than the stoichiometric ratio. Molar ratio of HF to the feed alkylbenzene is particularly important and must be at least 5, preferably 7 or higher, but a molar ratio above 15 is not necessary. Molar ratio of BF$_3$ to the feed alkylbenzene is at least 0.8, preferably 1.1–2.0. Optimum molar ratios of HF and BF$_3$ to the feed alkylbenzene slightly depend upon species of the feed alkylbenzene, etc.

Reaction temperature is a necessary factor for suppressing undesirable side reactions, because the formylation rate by CO is not considerably influenced by temperature, whereas such reaction as disproportionation, etc. of alkylbenzene is very sensitively accelerated by temperature. The present process does not require such an extremely low, economically disadvantageous temperature as so far required to avoid the complexing reaction or considerably reduce the influence of complexing reaction, but it is preferable to carry out the formylation reaction somewhat at a low temperature to improve the yield.

On the other hand, the formylation reaction is exothermic, and it is desired to carry out the formylation reaction at a temperature as high as possible to facilitate the heat removal from the reactor. In practice, a maximum allowable temperature from the viewpoint of yield is employed as the reaction temperature. Thus, the reaction temperature greatly depends upon the reactivity of side reaction. When a raw material very sensitive to disproportionation reaction such as isopropylbenzene (cumene) is used, optimum reaction temperature is between $-10°$ C. and $-35°$ C., and when ethylbenzene or orthoxylene is used as a raw material, optimum temperature is between $+5°$ C. and $-20°$ C.

Any reactor can be used in the present invention, so far as it can attain a good gas-liquid contacting effect and removal of the heat of reaction. For example, a reactor of complete mixing type, such as a stirring tank, a reactor of piston flow type such as a pipe reactor, or a combination thereof can be used. Residence time in the reactor depends upon the type of reactor, but practically is in a range of 10–100 minutes for continuous operation.

Reaction product can be separated from HF—BF$_3$ in the reaction product solution withdrawn from the reactor, and recovered. For example, it is practical to heat the reaction product solution to decompose it, while vaporizing, separating and recyclically using HF—BF$_3$. A product with a satisfactory purity can be obtained by separating unreacted compound, high boiling products, etc. from recovered oil by distillation.

The raw material applicable to the present process and the corresponding product aldehyde include:

| Raw material compound | Corresponding product aldehyde |
| --- | --- |
| Toluene | 4-Methylbenzaldehyde (paratolualdehyde) |
| Ethylbenzene | 4-Ethylbenzaldehyde (paraethylbenzaldehyde) |
| o-Xylene | 3,4-Dimethylbenzaldehyde |
| m-Xylene | 2,4-Dimethylbenzaldehyde |
| Cumene | 4-i-Propylbenzaldehyde |
| Pseudocumene | 2,4,5,-Trimethylbenzaldehyde |
| Mesitylene | 2,4,6-Trimethylbenzaldehyde |
| n-Butylbenzene | n-Butylbenzaldehyde |

According to the present invention, paraethylbenzaldehyde, cuminaldehyde, and other aromatic aldehydes can be commercially produced. They are valuable as raw materials for perfume, and organic chemicals. It has been so far difficult to carry out their commercial production including processes. Thus, the significance of the present invention is very great.

One embodiment of carrying out the present process will be described, referring to the accompanying drawing.

FIGURE is a flow diagram showing one embodiment of the present process.

As shown in FIGURE, feed alkylbenzene is supplied to reactor 1 through line 3. Feed CO gas is supplied to reactor 1 through line 4 provided with pressure control valve 2 so that the partial pressure of CO in reactor 1 can be kept constantly under a specific pressure, that is, indirectly so that the total pressure in reactor 1 can be kept constant. If necessary, the inert gas accumulated in reactor 1 is purged to the outside of reactor 1 through line 16. Reaction solution is recycled in reactor 1 through cooler 5 to remove the heat of reaction and keep the temperature of reaction solution constant. The reaction solution is withdrawn to decomposition column 9 through line 8, where the reaction solution is decomposed by heating through heater 10 at the bottom of decomposition column, and released HF and BF$_3$ are separated into the top of decomposition column. The BF$_3$ and HF are passed through cooler 12, where the HF is condensed into a liquid state, while the BF$_3$ remains in a gaseous state. The gaseous BF$_3$ is returned to reactor 1 through line 6 by recycle compressor 11, while the liquid HF is once stored in storage tank 13 and returned to reactor 1 through line 7 by recycle pump 14. Feed ratio of the feed alkylbenzene to catalyst HF—BF$_3$ to reactor 1 is kept at a specific value.

The product aldehyde is withdrawn from the decomposition column at the bottom, and recovered as bottoms through line 15, and led to alkali-water washing means 17 to remove the acid remaining in a small amount. Then, the bottoms is successively distilled through distillation columns 18 and 19, whereby low boiling compounds such as unreacted raw material, etc. are separated through line 20, high boiling compounds such as aldehyde degradation products, etc. are separated through line 21, and product aldehyde is recovered through line 22.

The present invention will be described in detail, referring to Examples.

EXAMPLE 1

A stainless steel autoclave with a net capacity of 1 l, provided with a stirrer was used as a formylation reactor, to which 3.0 moles per hour of feed cumene, 30 moles per hour of catalyst HF and 3.7 moles per hour of catalyst $BF_3$ were supplied under stirring in a state pressurized by CO to a total pressure of 20 kg/cm² gage. Reaction temperature was controlled to constant $-25°$ C. by cooling through the jacket around the reactor, and reaction solution was continuously withdrawn from the reactor so that the liquid level in the reactor could be kept constant. During the reaction, CO was continuously supplied to the reactor through a pressure control valve without interruption so that the pressure in the reactor could be kept constant. Partial pressure of CO in the reactor was kept under constant 18 kg/cm² absolute during the stationary period of reaction. p-Isopropylbenzaldehyde was formed in 79% yield based on the feed cumene in the oil obtained by separating the catalyst from the reaction solution. Cuminaldehyde with 99% purity was obtained by separating the unreacted raw material, high boiling compounds, etc. from it.

EXAMPLES 2 AND 3

Formylation reaction was carried out with the same feed cumene in the same manner as in Example 1, except that reaction conditions were changed. The conditions and results are shown in Table 1, together with those of Example 1.

TABLE 1

| Production of p-isopropylbenzaldehyde (cuminaldehyde) | | | |
|---|---|---|---|
| | Ex. 1 | Ex. 2 | Ex. 3 |
| Reaction conditions unit | | | |
| Reaction pressure Kg/cm² gage | 20 | 15 | 20 |
| CO partial Kg/cm² absolute pressure | 18 | 12 | 17 |
| Reaction temperature °C. | −25 | −30 | −20 |
| Feed rate | | | |
| Cumene Mol/Hr | 3.0 | 3.0 | 3.0 |
| Hf Mol/Hr | 30 | 30 | 30 |
| $BF_3$ Mol/Hr | 3.7 | 3.8 | 3.6 |
| $BF_3$/Cumene by mole | 1.23 | 1.27 | 1.20 |
| Results | | | |
| Aldehyde yield*¹ Mol % | 79.0 | 75.0 | 77.0 |
| Percent feed dis- Mol % proportionation*² | 10.2 | 14.0 | 12.5 |

*¹Yield of cuminaldehyde based on feed cumene
*²Percentage of cumene lost by disproportionation reaction to feed cumene

COMPARATIVE EXAMPLE 1

A complexing reactor with a net capacity of 0.5 l was provided separately from the reactor of Example 1, and the cumene, HF and $BF_3$ were prepared into a complex solution at a temperature of $-25°$ C. in advance in the complexing reactor, and then the complex solution was supplied to the formylation reactor of Example 1, and then the formylation was carried out in the same manner and under the same conditions as in Example 1.

Cuminaldehyde yield based on the feed cumene was 27%, and 60% of feed cumene was disproportionated, producing a large amount of benzene, diisopropylbenzene, triisopropylbenzene and their formylated products. It was difficult to recover cuminaldehyde from the mixture.

EXAMPLES 4, 5 AND 6 p-Ethylbenzaldehyde was produced from ethylebenzene in the same manner as in Example 1. Reaction conditions and results are shown in Table 2. Product ethylbenzaldehyde could be easily isolated and contained about 1.5% of o-ethylbenzaldehyde.

TABLE 2

| Production of ethylbenzaldehyde | | | |
|---|---|---|---|
| | Ex. 4 | Ex. 5 | Ex. 6 |
| Reaction condition unit | | | |
| Reaction pressure Kg/cm² gage | 15 | 10 | 15 |
| CO partial Kg/cm² absolute pressure | 13 | 8 | 12 |
| Reaction temperature °C. | 0 | 0 | 5 |
| Feed rate | | | |
| Ethylbenzene Mol/Hr | 5.0 | 5.0 | 4.0 |
| HF Mol/Hr | 35.0 | 35.0 | 36.0 |
| $BF_3$ Mol/Hr | 5.8 | 5.5 | 4.4 |
| $BF_3$/Ethylbenzene by mole | 1.16 | 1.10 | 1.10 |
| Results | | | |
| Ethylbenzaldehyde Mol % | 68.0 | 65.0 | 78.0 |
| Percent feed dis- Mol % proportionation | 2.0 | 3.0 | 1.5 |

COMPARATIVE EXAMPLE 2

An ethylbenzene complex with HF—$BF_3$ was prepared in advance in the same manner as in Comparative Example 1 except that the complexing temperature was 0° C., and then the resulting complex was formylated in the same manner and under the same conditions as in Example 4. It was found that 50% of feed ethylbenzene was disproportionated, and ethylbenzaldehyde based on feed ethylbenzene was only 40%.

EXAMPLES 7 AND 8

3,4-Dimethylbenzaldehyde was produced from o-xylene in the same manner as in Example 1. Reaction conditions and results are shown in Table 3.

TABLE 3

| Production of 3,4-dimethylbenzaldehyde | | |
|---|---|---|
| | Ex. 7 | Ex. 8 |
| Reaction condition unit | | |
| Reaction pressure Kg/cm² gage | 15 | 10 |
| CO Partial Kg/cm² absolute pressure | 15 | 10 |
| Reaction temperature °C. | 0 | 0 |
| Feed rate | | |
| o-xylene Mol/Hr | 5.0 | 5.0 |
| HF Mol/Hr | 30.0 | 35.0 |
| $BF_3$ Mol/Hr | 6.0 | 5.5 |
| $BF_3$/o-xylene by mole | 1.20 | 1.10 |
| Results | | |
| Aldehyde yield*³ Mol % | 78.0 | 82.0 |
| Selectivity*⁴ Mol % | 99.0 | 99.0 |

*³Yield of dimethylbenzaldehyde based on feed o-xylene
*⁴Percentage of 3,4-isomer in dimethylbenzaldehyde

COMPARATIVE EXAMPLE 3 o-Xylene was complexed with HF—$BF_3$ in advance, and then the resulting complex was formylated in the same manner and under the same conditions as in Example 7. In the complexing reaction, o-xylene was isomerized to m-xylene, and the formylation product of m-xylene, i.e. 2,4-dimethylbenzaldehyde was inevitably contained in the product in a considerable proportion.

What is claimed is:

1. A process for continuously producing cuminaldehyde by formylation of cumene with carbon monoxide in the presence of hydrogen fluoride-boron trifluoride, which comprises introducing a raw material cumene into the reactor while maintaining a partial pressure of the carbon monoxide of 10-30 kg/cm$^2$ absolute and a temperature between $-10°$ C. and $-35°$ C., thereby effecting complexing of the cumene with hydrogen fluoride-boron trifluoride and formylation of the cumene with the carbon monoxide continuously in the reactor.

2. A process according to claim 1, wherein the hydrogen fluoride is introduced into the reactor at a molar ratio of the hydrogen fluoride to the cumene of at least 5.

3. A process according to claim 1, wherein the hydrogen fluoride is introduced into the reactor at a molar ratio of the hydrogen fluoride to the cumene of 7-15.

4. A process according to claim 1, wherein the boron trifluoride is introduced into the reactor at a molar ratio of the boron trifluoride to the cumene of at least 0.8.

5. A process according to claim 4, wherein the boron trifluoride is introduced into the reactor at a molar ratio of the boron trifluoride to the cumene of 1.1-2.0.

6. A process according to claim 1 wherein the boron trifluoride is dissolved in the hydrogen fluoride in the reactor and carbon monoxide is introduced into the reactor prior to introducing the cumene into the reactor.

7. A process according to claim 6 wherein following introduction of the cumene into the reactor, carbon monoxide is continuously supplied to the reactor to maintain the partial pressure of the carbon monoxide at at 10-30 kg/cm$^2$ absolute, hydrogen fluoride and boron trifluoride are continuously supplied to the reactor, cumene is separately and continuously supplied to the reactor, and cuminaldehyde is withdrawn from the reactor.

* * * * *